United States Patent [19]

Condie et al.

[11] 3,998,946
[45] Dec. 21, 1976

[54] FIBRINOGEN-FREE PLASMINOGEN-PLASMIN-FREE PLASMA AND METHOD OF PREPARING AND USING SAME

[75] Inventors: Richard M. Condie, Minneapolis; Luis H. Toledo-Pereyra, Hopkins, both of Minn.

[73] Assignee: The Regents of the University of Minnesota, Minneapolis, Minn.

[22] Filed: Apr. 23, 1975

[21] Appl. No.: 570,569

[52] U.S. Cl. ............................................. 424/101
[51] Int. Cl.² .................. A61K 35/16; A61K 35/14
[58] Field of Search .................................... 424/101

[56] References Cited
OTHER PUBLICATIONS

Stephan et al., Chem. Abst., vol. 69 (1968), p. 17412h.

Primary Examiner—Sam Rosen
Attorney, Agent, or Firm—Burd, Braddock & Bartz

[57] ABSTRACT

A method of treating blood plasma or fractionated plasma products with fumed colloidal silica to remove fibrinogen without polymerization to fibrin, to remove the plasminogen-plasmin proteolytic enzyme system, to remove cholesterol and lipoproteins and reduce triglycerides, while maintaining plasma coagulation factor II at pretreatment levels and leaving immunoglobulins and other protein constitutents unaffected, and the resulting product. Plasma products treated with fumed silica may be subjected to long-term storage for a year or more without loss of its biologically active support properties, thereby circumventing the problem of hepatitis. The treated plasma products, either fresh or after long-term storage, may be used as a perfusion support media for organ perfusion, for treatment of hemmorrhagic shock and similar purposes for which untreated plasma and fractionated plasma products are customarily used, with equal or superior effectiveness.

2 Claims, 2 Drawing Figures

FIBRINOGEN-FREE PLASMINOGEN-PLASMIN-FREE PLASMA AND METHOD OF PREPARING AND USING SAME

The invention described herein was made in the course of work under a grant or award from the Department of Health, Education and Welfare.

This invention is directed to a fibrinogen-free plasminogen-plasmin-free blood plasma product and to the method of making such a product by the treatment of animal blood plasma or fractionated plasma products with a pure synthetic fumed colloidal silicon dioxide containing siloxan and silanol groups on its surface. It has been found that fumed silica treated plasma product retains its biological support properties through longterm storage and is useful in organ perfusion, treatment of shock, and the like, while circumventing the transmission of hepatitis in untreated plasma.

BACKGROUND OF THE INVENTION

With the advent of clinical organ transplantation as an accepted method of treatment for various diseases, the need for preservation of cadaver organs became established. The requirements of a media that will support organ perfusion were partially accomplished by the use of cryoprecipitated plasma (CPP). Thus, the problems associated with blockage of capillaries by lipoproteins, fibrin aggregates, and the like, were to a certain degree prevented. There are, however, several disadvantages related to the use of CPP: (a) it is difficult to standardize and store; (b) it must be thawed and filtered immediately before use; and (c) there is a risk of transmission of hepatitis in the use of unstored plasma. Most important, it is not reliable for long-term perfusion since renal function does not reliably and immediately reappear upon transplantation of kidneys preserved for more than 48 hours.

A number of efforts have been made to eliminate some of these disadvantages. In particular, the use of synthetic plasma derivatives and albumin solutions have been tried. Such solutions theoretically should contain little aggregated materials, i.e., lipoproteins and partially polymerized fibrinogen and since they can be stored there is little risk of hepatitis. However, for unknown reasons these materials are not as satisfactory as plasma. In applicants' laboratory at the University of Minnesota Medical School, canine kidneys perfused with albumin demonstrated only 50 percent survival after 48 hours preservation. Furthermore, only 25 percent of the kidneys perfused with plasmanate survived after the same preservation period.

One possible explanation why CPP is superior to the other plasma derivatives for organ perfusion is the trace materials within plasma which are necessary for metabolic maintenance of the hypothermic kidney. Such materials may be removed by the processing of albumin or plasmanate. At the same time it may be possible that the problem with CPP is related to the failure to remove by freezing all of the precipitable and denaturable elements within the plasma.

The picture for shock is even less clear. Upon storage, plasma and blood lose their effectivenss as plasma expanders in hypovolemic and endotoxic shock. Serum, the protein fluid remaining after the polymerization of fibrinogen, is of little value in organ perfusion and may be even toxic, whereas, in shock, even saline is more effective than serum, suggesting that in the clotting of blood harmful pharmacological active factors may be generated.

The deficiencies in the above mentioned preparations led to the investigation and development of the method of the present invention for (1) removing fibrinogen from plasma without its polymerization to fibrin and leaving prothrombin at pretreatment levels, (2) removing the plasminogen-plasmin proteolytic enzyme system, (3) without generation of toxic factors nor removal of biologically essential support factors, and (4) allowing for long-term storage of plasma without loss of its biological support properties.

A series of investigations with various natural and synthetic poly-silica compounds, resulted in the discovery that a synthetic fumed colloidal silicon dioxide could be used to treat plasma removing fibrinogen without polymerization, and preventing the accumulation of pharmacologically active toxic split products. Subsequent research led to the discovery that in addition the proteolytic enzyme system plasminogen-plasmin is also removed by fumed silica treatment. Plasma treated and processed in this manner has been extensively tested in both animal and human models and evaluated for efficacy for organ preservation, shock, and for retention of its biological support properties following long-term storage (1 year).

Blood contains plasminogen, the inactive precursor of the potent proteolytic enzyme plasmin. Under ordinary conditions such as those involved in the preparation of plasma from citrated whole blood, plasminogen is not activated in any detectable quantities since there are inhibitors in plasma which can act to block activation by kinases as well as inhibitors that can block the action of the enzyme plasmin. However, on long-term storage of plasma there apparently is some activation of plasminogen to plasmin (up to 5 percent) and the subsequent proteolysis of fibrinogen, immunoglobulins, and other proteins. With plasma develops visible aggregates which are presumably products of partially degraded fibrinogen and immunoglobulins. This problem is largely circumvented by the outdating of plasma, resulting in discarding and loss of a valuable resource.

In the classic Cohn alcohol fractionation of human plasma, the plasminogen is concentrated and freed of its inhibitors in the fraction process. The result is that fractions I, II, III of the Cohn procedure contain much greater quantities of plasminogen than are present initially in plasma. The presence of high concentrations of plasminogen, if activated, leads directly to the degradation of fibrinogen to form the toxic so-called split products. In addition, it has been demonstrated that the plasmin system can partially degrade the immunoglobulins, a process which leads to formation of molecular aggregates.

Immunoglobulins acted upon by plasmin when injected into the circulation are eliminated very rapidly when compared to normal, unaltered immunoglobulins. The net effect is to prevent the attainment of high blood levels that are necessary in treating bacterial, toxic states and viral diseases. In particular, the plasmin altered immunoglobulin when administered to immune deficiency patients intravenously produce anaphylactoid-like reactions, thereby eliminating a potentially effective method of treating such patients.

A major obstacle to the preparation of potent solutions of purified immunoglobulins that can be safely administered intravenously to patients to achieve high blood levels in treating immune defects and life threatening infections has been the failure to either eliminate or prevent the aggregation of immunoglobulins during purification. Aside from the fact that the universally employed Cohn alcohol method of plasma protein fractionation may irreversibly denature some plasma proteins, the presence of the plasma proteolytic enzyme plasminogen has been demonstrated to attack, and particularly degrade by its proteolytic activity, immunoglobulins, particularly the IgG class. The IgG immunoglobulins that have been attacked by plasmin form molecular aggregates which have been implicated in the activation of the kinen and complement systems and further, when their aggregated solutions are administered intravenously to patients with immune deficiency, precipitate anaphylactoid systemic reactions. In addition, these partially degraded aggregated IgG preparations are rapidly eliminated from the circulation thereby significantly reducing the effectiveness of specific antibody in conferring protection to toxic states resulting, for example, form diphtheria toxin, and protection against infection. Thus, the hoped for goal of achieving high effective blood levels of a biologically active antibody to toxins, viral or bacterial organisms have not been attained to date.

DESCRIPTION OF THE PRIOR ART

In the past there has been no single process that would remove both lipoproteins and fibrinogen without polymerizing to fibrin. Cryoprecipitation of plasma has been extensively utilized in the removal of some lipoprotein aggregates and some polymerized fibrinogen. Serum separated from clotted whole blood has very low levels of fibrinogen but it is actually toxic in organ perfusion, and harmful in hypovolemic and endotoxic shock.

Intravenous preparations of purified immunoglobulins have been prepared but have all produced reactions when administered intravenously to the immune deficient patient. One preparation prepared by enzymatic treatment with trypsin of IgG, while producing fewer reactions when administered intravenously, had greatly reduced half life. It is presumed that the major obstacles to preparation of a highly purified intravenous IgG has been the presence of plasminogen-plasmin contaminating the early fractionation stages during purification of the immunoglobulins. The major approach to dealing with the plasminogen problem has been the addition of compounds which do not remove the enzyme precursor or its activated plasmin but inhibit the activation of the plasminogen to plasmin. This has come about by application of the fact that E amino caproic acid combines and inhibits the activation of plasminogen to plasmin. It is not clear, however, that this process offers much in the large scale production and preparation of plasminogen-free plasma that could be used in preparing aggregate-free plasma protein of high purity, particularly since it has not been demonstrated conclusively that plasmin is inhibited by E amino caproic acid. Purification by chromatography could remove plasminogen. However, it is much more desirable that a process be developed where whole plasma could be treated economically and with ease and in a manner that plasminogen and plasmin could be removed in the early phases of preparation when the active and potent plasma inhibitors of the plasminogen activation system are present and effective in the whole plasma.

Synthetic fumed silicon dioxide has been used to remove lipoproteins, cholesterol and triglycerides from serum. However, we have demonstrated that treating plasma with synthetic fumed silicon dioxide removes lipoproteins, cholesterol and triglycerides and, at the same time, removes fibrinogen by mechanisms not involving polymerization of fibrinogen to fibrin since the prothrombin remains at pretreatment levels, and removes the plasminogen-plasmin system.

SUMMARY OF THE INVENTION

Broadly stated, the invention comprises the method of treating blood plasma or plasma fractions, human or non-human, in the course of normal processing with pyrogenic or fumed silica (colloidal synthetic silicon dioxide of highest purity containing siloxan and silanol groups on its surface), in either wet or dry form, followed by separation of the silica, the resulting fibrinogen-free plasminogen-plasmin-free plasma products, and methods of using those products.

The results of this method of plasma treatment provides plasma that can be stored for two years or more without loss in its biological support activities for treatment of hemorrhagic and endotoxic shock and as a support media for organ perfusion. The advantages of long-term storage provides an opportunity for extensive testing, circumventing of hepatitis problems and successful pooling of a valuable natural resource.

BRIEF DESCRIPTION OF THE DRAWINGS

The invention is illustrated in the accompanying drawings in which.

DESCRIPTION OF THE PREFERRED EMBODIMENTS

Figure 1:
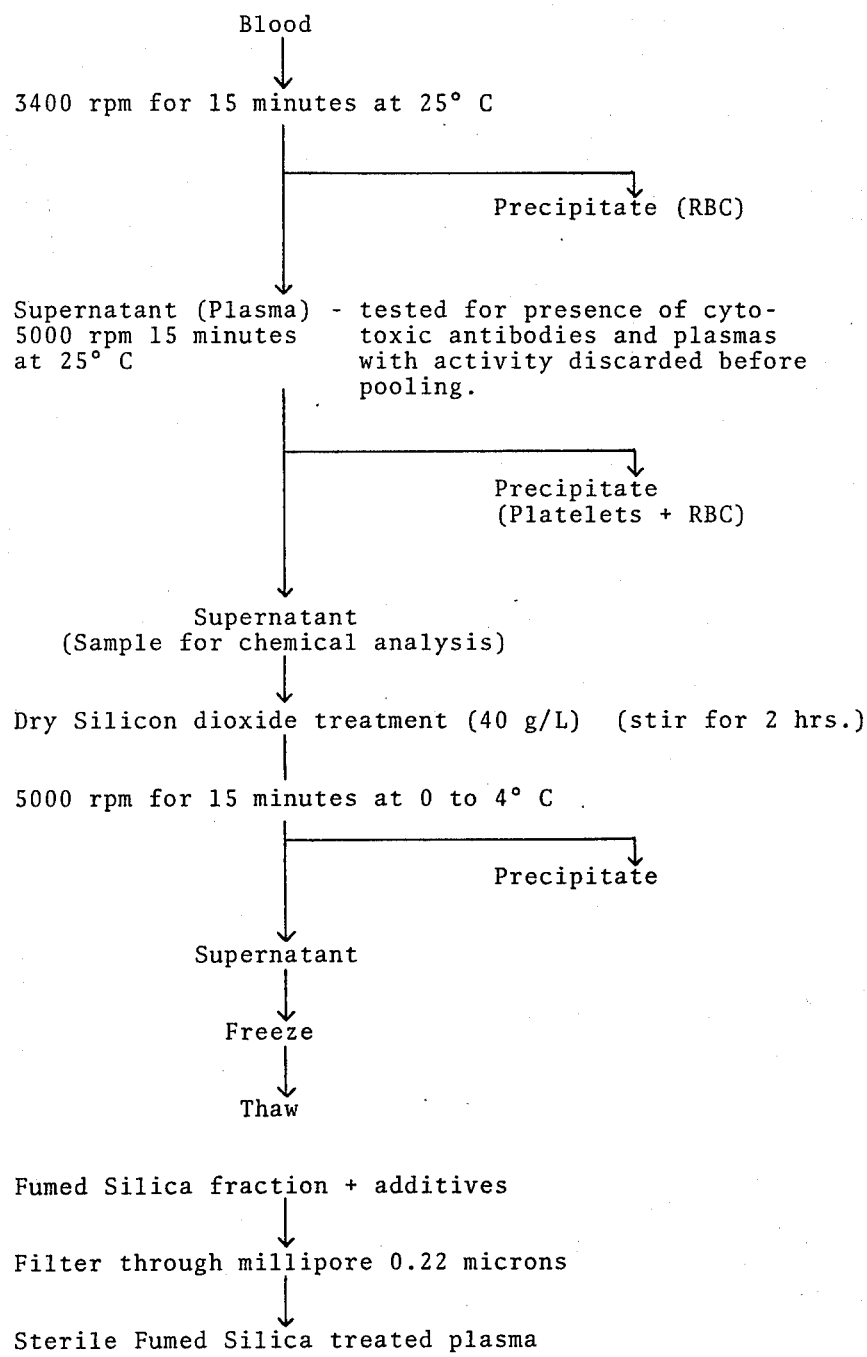
FIG. 1 is a flow sheet showing the method of preparing fumed silica treated plasma using dry silica.

Referring now to the drawings, and particularly to FIG. 1, there is illustrated in flow sheet form a preferred method for preparing fumed silicon dioxide treated plasma using dry fumed silica. The drawn blood is first treated in the coventional manner by centrifuging at about 3400 rpm for about 15 minutes at about 25° C. The precipitate consisting predominantly of red blood cells is separated. The plasma, the supernatant fraction, is tested for the presence of cytotoxic antibodies. Any plasma with such activity is discarded. The remaining blood is pooled for further processing. The plasma is centrifuged at about 5000 rpm for about 15 minutes at about 25° C. The precipitate composed predominantly of platelets and red blood cells is again separated. A sample of the supernatant plasma is withdrawn for chemical anaylsis.

Sterile dry colloidal fumed silicon dioxide of the highest purity is then added to the plasma at room temperature with stirring to a final concentration of between about 10 to 50 and preferably about 25 to 40 gram of silica per liter of plasma. Exemplary pyrogenic or fumed silicas which may be used are those sold under the brand name Aerosil 380 by Degussa, Inc., New York, N.Y., and under the brand name Cab-O-Sil by Cabot Corp., Boston, Mass. The plasma and silica are stirred for from about 20 minutes to 2 hours from 4° C to 37° C but preferably at room temperature, and then centrifuged at about 100 to 10000 rpm for about 10 to 30 minutes, preferably at about 5000 rpm for about 15 minutes, at a temperature in the range between about 0° to 37° C, preferably about 0° to 4° C. The precipitate comprising the silica and removed constituents is again separated and the supernatant plasma may optionally be frozen for storage. Any desired additives may be admixed. The product is filtered through a 0.22 micron bacterial filter and is ready for use or storage under sterile conditions without preservatives either at room temperature or at 4° C. Although centrifugal separation is preferred, the supernatant liquid may be separated by filtration.

Figure 2:
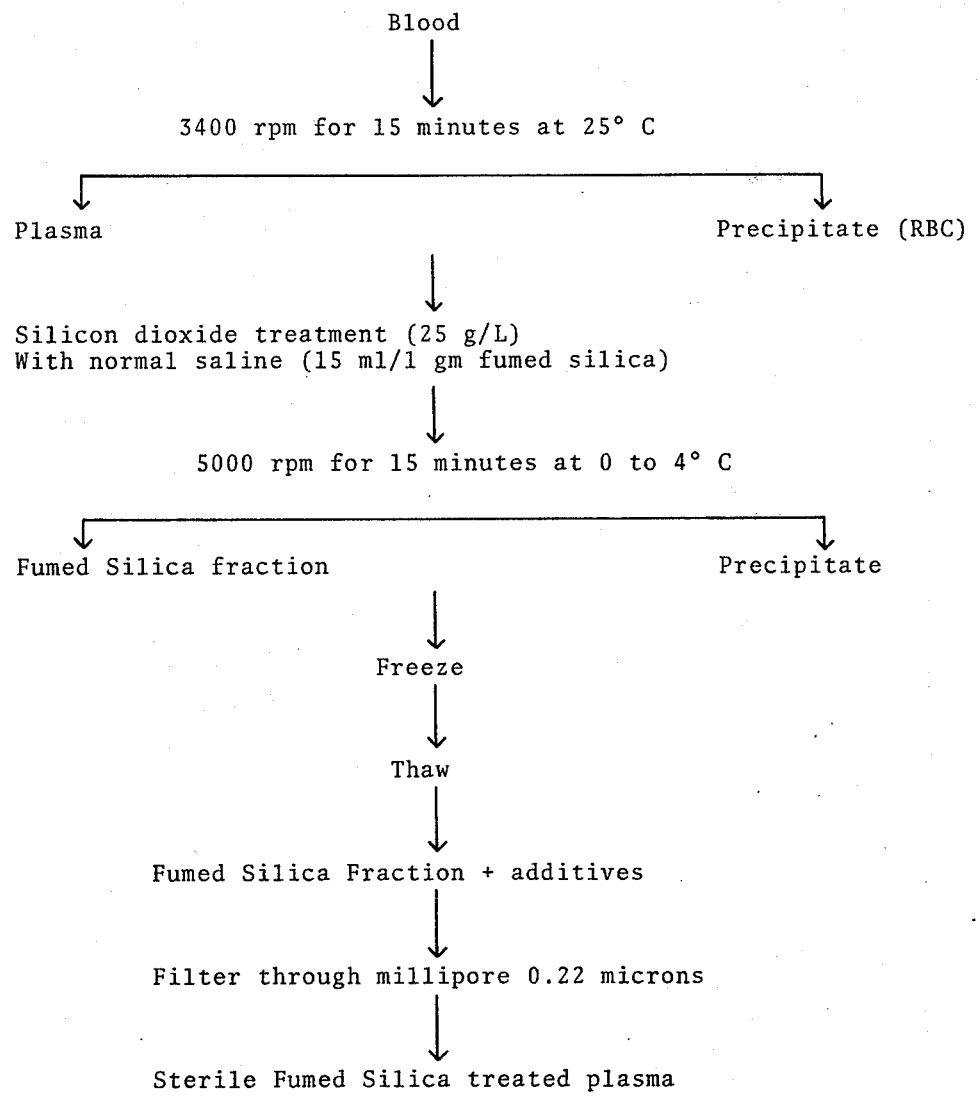
FIG. 2 is a flow sheet showing a modified form of treatment utilizing saline wetted fumed silica.

According to the modified form of treatment illustrated in FIG. 2, the drawn blood is centrifuged at about 3400 rpm for about 15 minutes at about 25° C and the precipitate separated. After testing and pooling, sterile fumed silica in admixture with normal saline in concentration of about 1 gram silica per 15 milliliters of saline solution is added to the plasma with stirring at room temperature to a final concentration between about 10 to 50 and preferably about 25 to 50 grams silica per liter of plasma. The mixture is stirred from 20 minutes to 2 hours and thereafter centrifuged or filtered, as described. The silica treated supernatant fraction, after separation of the precipitate, is handled as previously described.

Horse, dog, rabbit and human plasma have been treated with fumed silica according to the described methods. The treatment of plasma in this manner completely removes fibrinogen without liberation of split products or other pharmacologically active poly-peptide products. It removes the plasminogen-plasmin proteolytic enzyme system. It removes all of most of the aggregateable beta-lipoproteins and thermo-denaturable lipoproteins, fats and lipids, i.e., cholesterol, triglycerides, etc. In addition, the fumed silicon dioxide has been shown to remove bacteria and herpes virus, traces of red blood cell membranes, white blood cells and platelets. The addition of fumed silica to plasma does not have any effect on concentrations and activities of the enzymes LDH, SGOT, and beta-glucuronidase, nor does it modify the level or activities of the immunoglobulins IgG, IgM, IgA. Plasma coagulation factor II is left at pretreatment level.

The removal of those most labile materials which on storage at 4° or 25° C either are denatured or form aggregates permit long-term storage of the silica treated plasma without loss of the biologically active support properties of the plasma. A comparative chemical analysis of untreated dog plasma with cryoprecipitation treated plasma and silica treated plasma is shown in Table I.

Extensive testing has been conducted in both animal and human models to evaluate the efficacy of fumed silica treated plasma for use in organ preservation, treatment of shock, and for retention of biological support properties following long-term storage. These studies demonstrate that silica treated plasma is superior to CPP in the preservation of dog kidneys for 48 to 120 hours. Furthermore, silica treated plasma stored for one year at room temperature still served as a superior perfusate during 48 hour preservation. In dog kidneys perfused by hypothermic pulsatile perfusion for 48 hours to 120 hours comparing the silicon dioxide treated plasma with standard cryoprecipitated plasma (CPP), it was revealed that the chemical characteristics of the perfusate and the physical characteristics of perfusion were more stable when silicon dioxide treated plasma was used. Survival was consistently better following autotransplantation of the preserved kidney and contralateral nephrectomy when the perfusate was silicon dioxide treated plasma. Two of eight kidneys perfused for 120 hours with silicon dioxide treated plasma had returned to normal renal function by 18 days after autotransplantation. Perfusion was according to the system of Moberg et al described in Lancet, 1971, 2:1403. These results are reported in *Surgery, Gynecology & Obstetrics*, June 1974, Vol. 138, pp. 910–905, incorporated herein by reference.

The finding that fumed silica treatment of plasma removes the plasminogen-plasmin system in addition to fibrinogen, cholesterol, fatty acids, lipoproteins, etc. offers additional evidence explaining the superior nature of this processed plasma in organ perfusion. The presence of activatable plasminogen in plasma could among other things lead to the formation of aggregated immunoglobulins, fibrin or fibrinogen split products and the release of pharmacologically active peptides. A more critical factor is the possibility that plasminogen activated by urokinases released from the kidney during perfusion, would activate all the plasminogen resulting in the injury of the endothelial lining of the capillary vessel, which in turn could lead to areas of clot formation at the time the perfused kidney is transplanted and circulation reconstituted.

In the light of findings that use of fumed silica treated plasma results in considerable improvement of the support media for long-term perfusion, as compared with cryoprecipitated plasma, attention was directed to the use of silica treated plasma in the treatment of hypovolemic shock in dogs. Mongrel dogs weighing between 17 to 24 kg were anesthetized with sodium methohexital for induction and halothane for mainte-

TABLE I

COMPARATIVE CHEMICAL ANALYSIS OF THE DOG PLASMA TREATED WITH CRYOPRECIPITATION ALONE AND THE DOG PLASMA EXTRACTED WITH FUMED SILICA (Mean values ± SE)

| Chemical Constitution | Untreated Plasma | Cryoprecipitated Plasma | Silica Fraction |
|---|---|---|---|
| Cholesterol (mg%) | 100.7 ± 15.3 | 88.7 ± 9.6 | 0 |
| Triglycerides (mg%) | 59.9 ± 11.5 | 62.8 ± 8.5 | 20.3 ± 6.5 |
| Fibrinogen (mg%) | 0.41 ± 0.17 | 0.26 ± 0.11 | 0 |
| α-Lipoproteins | Normal trace | Normal trace | 0 |
| β-Lipoproteins | Normal trace | Normal trace | 0 |
| Free Fatty Acids (mEq/L) | 0.6 ± 0.2 | 0.4 ± 0.2 | 0.35 ± 0.15 |
| Total Proteins (gm%) | 3.2 ± 0.2 | 2.9 ± 0.3 | 3.1 ± 0.4 |
| Albumin (gm%) | 2.5 ± 0.2 | 1.8 ± 0.2 | 2.0 ± 0.3 |
| Globulins (gm%) | 0.6 ± 0.1 | 1.1 ± 0.2 | 1.1 ± 0.1 |
| Osmolarity (mOsm/L) | 292 ± 7.3 | 285 ± 5.3 | 290 + 6.7 |
| Sodium (mEq/L) | 139 ± 4.3 | 137 ± 5.2 | 140 ± 3.5 |
| Potassium (mEq/L) | 4.2 ± 0.4 | 4.3 ± 0.6 | 4.1 ± 0.6 |
| Chloride (mEq/L) | 99 ± 6.7 | 90 ± 6.5 | 100 ± 5.7 | nance. They were bled 60% of the blood volume in a one hour period until the systolic blood pressure was 40 mmHg. Thereafter, several groups of dogs were studied (8 dogs per group) according to the type of solution moval of fibrinogen is not by way of polymerization of fibrinogen to fibrin. Comparison of silicon dioxide treated plasma and untreated plasma and serum is shown in Table III.

TABLE III

FIBRINOGEN REMOVAL WITHOUT POLYMERIZATION TO FIBRIN BY TREATING PLASMA WITH A SYNTHETIC SILICON DIOXIDE

| Clotting Factor | Plasma (Normal Activity) | Fumed Silica Reacted Plasma (Per cent Recovery) | Serum (Per cent Recovery) |
| --- | --- | --- | --- |
| II | 78 | 103 | 36 |
| V | 100 | 4 | 24 |
| VII | 45 | 16° | 202 |
| X | 63 | 38 | 127 |
| VIII | 71 | 4 | 4 |
| IX | 128 | 28 | 247 |
| XI | 77 | 5 | 247 |
| XII | 100 | 4 | 150 |
| $\phi$ (Split prod.) | 492 mg/100 ml | 0 | 0.19 |
| $\phi$* | 330 mg/100 ml | 0 | 0 |

*Radialimmunodiffusion utilized. All dogs but the control group received the same volume of plasma or blood extracted during bleeding. This volume was administered immediately following the one hour of continuous bleeding. Group I, no treatment was given; Group II, treated with Ringer's lactate; Group III, treated with dog plasma; Group IV, treated with human plasmanate; Group V, fresh whole blood plus 20% Ringer's lactate; Group VI, treated with dog's serum; and Group VII, treated with plasma prepared by fumed silica fractionation. The dog's survival was followed for at least three days post reinfusion. Daily IV infusion of 1,000 cc of Ringer's lactate was administered to all survivors. Thereafter, normal oral feeding was instituted. The results are tabulated in Table II. Silica treated plasma proved to be superior to other protein plasma fractions in the treatment of hypovolemic shock.

TABLE II

HEMORRHAGIC SHOCK

| | Groups | Survival |
| --- | --- | --- |
| I | Control - No Treatment | 12.5% (1/8) |
| II | Ringer's Lactate | 50.0% (4/8) |
| III | Plasma | 75.5% (6/8) |
| IV | Human Plasmanate | 62.5% (5/8) |
| V | Fresh Whole Blood and 20% Ringer's Lactate | 87.5% (7/8) |
| VI | Serum | 12.5% (1/8) |
| VII | Fumed Silica Fraction | 75.5% (6/8) |

There are several advantages of fumed silica treated plasma in relation to whole blood or plasma in the treatment of hemorrhagic shock; (1) it can be stored at warm or cold temperatures for long periods of time (one year or more) without deterioration of activity; (2) there are no bacteria found after sterilization and filtering; (3) although virus have not been identified, there is definite evidence the elimination of herpes simplex; and (4) there has been no sensitization observed. Therefore, these characteristics favor the use of silica treated plasma in the treatment of hemorrhagic shock.

Up to the present time, fibrinogen has only partially been removed from plasma by clotting, salt or alcohol fractionation. Treatment of plasma with the synthetic silicon dioxide removes fibrinogen without liberation of fibrin split products or consumption of prothrombin, the plasma coagulation factor II, indicating that re- It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. In the method of perfusing kidneys removed by nephrectomy to preserve the same pending transplantation into a living body, the improvement which consists in using as a perfusate a fumed silica treated fibrinogen-free, plasminogen-plasmin-free and lipoprotein and lipid-free blood plasma product produced by:

A. intimately admixing finely divided sterile fumed silica containing siloxan and silanol groups at its surface with a blood plasma product selected from the class consisting of blood plasma and plasma fractionation products containing fibrinogen, plasminogen-plasmin enzyme system and lipoproteins and lipids, and B. separating the silica and associated fibrinogen, plasminogen-plasmin, lipoprotein and lipids from the remaining plasma product.

2. In the method of treating hypovolemic (hemorrhagic) and endotoxic shock in living bodies, the improvement which consists in transfusing the body with a fumed silica treated fibrinogen-free, plasminogen-plasmin-free and lipoprotein and lipid-free blood plasma product produced by:

A. intimately admixing finely divided sterile fumed silica containing siloxan and silanol groups at its surface with a blood plasma product selected from the class consisting of blood plasma and plasma fractionation products containing fibrinogen, plasminogen-plasmin enzyme system and lipoproteins and lipids, and B. separating the silica and associated fibrinogen, plasminogen-plasmin, lipoprotein and lipids from the remaining plasma product.

* * * * *

UNITED STATES PATENT AND TRADEMARK OFFICE
CERTIFICATE OF CORRECTION

PATENT NO. : 3,998,946
DATED : December 21, 1976
INVENTOR(S) : Richard M. Condie et al It is certified that error appears in the above–identified patent and that said Letters Patent are hereby corrected as shown below:

Column 1, line 63, "effectivenss" should be --effectiveness--.

Column 2, line 38, after "With", --time-- is omitted.

Column 3, line 20, "form" should be --from--.

Column 6, line 27, "910" should be --901--.

Signed and Sealed this

Fifth Day of April 1977

[SEAL]

Attest:

RUTH C. MASON
Attesting Officer

C. MARSHALL DANN
Commissioner of Patents and Trademarks